United States Patent
Jackson et al.

(10) Patent No.: US 9,504,379 B2
(45) Date of Patent: Nov. 29, 2016

(54) METHOD AND APPARATUS FOR THE DETECTION OF IMPAIRED DARK ADAPTATION

(71) Applicant: THE UAB RESEARCH FOUNDATION, Birmingham, AL (US)

(72) Inventors: Gregory R Jackson, Hershey, PA (US); Cynthia Owsley, Birmingham, AL (US)

(73) Assignee: The UAB Research Foundation, Birmingham, AL (US)

( * ) Notice: Subject to any disclaimer, the term of this patent is extended or adjusted under 35 U.S.C. 154(b) by 0 days.

(21) Appl. No.: 14/706,536

(22) Filed: May 7, 2015

(65) Prior Publication Data

US 2015/0238077 A1    Aug. 27, 2015

Related U.S. Application Data

(60) Division of application No. 13/028,893, filed on Feb. 16, 2011, now Pat. No. 9,050,021, which is a continuation of application No. 12/886,264, filed on Sep. 20, 2010, now abandoned, which is a (Continued)

(51) Int. Cl.
| | | |
|---|---|---|
| A61B 3/02 | (2006.01) |
| A61B 3/06 | (2006.01) |
| A61B 3/00 | (2006.01) |
| G06F 19/00 | (2011.01) |

(52) U.S. Cl.
CPC ............ *A61B 3/063* (2013.01); *A61B 3/0008* (2013.01); *A61B 3/0025* (2013.01); *A61B 3/0033* (2013.01); *A61B 3/0041* (2013.01); *A61B 3/0083* (2013.01); *A61B 3/0091* (2013.01); *G06F 19/345* (2013.01)

(58) Field of Classification Search
CPC .... A61B 3/024; A61B 3/032; A61B 3/1015; A61B 3/103; A61B 3/113
USPC ................................ 351/200, 203, 224, 246
See application file for complete search history.

(56) References Cited

U.S. PATENT DOCUMENTS

| | | |
|---|---|---|
| 2,247,653 A | 1/1938 | Feldman |
| 3,891,311 A | 6/1975 | Fletcher |

(Continued)

FOREIGN PATENT DOCUMENTS

GB          530308          10/1940

OTHER PUBLICATIONS

US 2,239,264, 01/1941, Wigelsworth (withdrawn).
Scilley, Kay et al. "Early Age-Related Maculopathy and Self-Reported Visual Difficulty in Daily Life" Opthamology, 109(7), Jul. 2002, Elsevier Science, Inc.
Reeves, et al. "The effect of photon noise on the detection of white flashes" Vision Research Pergamon Press, Oxford, GB, vol. 38, No. 5, Mar. 1, 1998, pp. 691-703, XP022261571, ISSN: 0042-6989.

(Continued)

*Primary Examiner* — James Greece
(74) *Attorney, Agent, or Firm* — Thomas G. Peterson; Bradley Arant Boult Cummings LLP

(57) ABSTRACT

The present method describes a new method for the measurement of dark adaptation. The dark adaptation status of subjects may then be used to identify those subjects who are at risk of developing and/or who are currently suffering from a variety of disease states having their clinical manifestations in impaired dark adaptation. The disease states include, but are not limited to, age related macular degeneration, vitamin A deficiency, Sorsby's Fundus Dystrophy, late autosomal dominant retinal degeneration, retinal impairment related to diabetes and diabetic retinopathy. An apparatus for administering the test method described is also provided.

47 Claims, 5 Drawing Sheets

Related U.S. Application Data continuation of application No. 12/391,829, filed on Feb. 24, 2009, now Pat. No. 7,798,646, which is a division of application No. 10/571,230, filed as application No. PCT/US2004/029003 on Sep. 3, 2004, now Pat. No. 7,494,222.

(60) Provisional application No. 60/500,163, filed on Sep. 4, 2003.

(56) References Cited

U.S. PATENT DOCUMENTS

| | | | |
|---|---|---|---|
| 4,545,658 A | | 10/1985 | Weiss |
| 5,080,478 A | | 1/1992 | O'Brien |
| 5,715,334 A | * | 2/1998 | Peters .......................... 382/254 |
| 5,822,037 A | | 10/1998 | Barad |
| 6,315,412 B1 | | 11/2001 | Snodderly |
| 6,478,424 B1 | | 11/2002 | Grinvald et al. |
| 6,895,264 B2 | * | 5/2005 | Rice et al. .................... 600/319 |
| 2006/0200013 A1 | | 9/2006 | Smith |
| 2007/0121071 A1 | * | 5/2007 | Jackson et al. ............... 351/246 |

OTHER PUBLICATIONS

Cideciyan, et al. "Rod plateaux during dark adaptation in Sorsby's fundus dustrophy and vitamin A deficiency" Investigative Ophthalmology and Visual Science, vol. 38, No. 9, 1997, pp. 1786-1794, XP002528782, ISSN: 0146-0404.

European Patent Office, European Search Report for Application No. 04783299.3, Jun. 4, 2009.

Hecht, et al. "The Dark Adaptation of Retinal Fields of Different Size and Location" The Journal of General Physiology; Nov. 20, 1935; pp. 321-337.

Lamb, T.D. "The Involvement of Rod Photoreceptors in Dark Adaptation" Vision Research; 1981; vol. 21; pp. 1773-1782.

Jackson, Gregory R., et al. "Section 5 Aging and dark adaptation" Vision Research 39 (1999) pp. 3975-3982.

Murray, Ian J. "Third Party Observation for application No. EP20040783299" European Patent Office; Jan. 22, 2015; pp. 1-3.

Ohba, et al. "Adaptation of the Pupil Light Reflex" Vision Research; vol. 12, pp. 953-967, 1971, Pergamon Press; Gret Britain.

European Patent Office, European extended search report for application No. 11186355, Feb. 10, 2012.

* cited by examiner

METHOD AND APPARATUS FOR THE DETECTION OF IMPAIRED DARK ADAPTATION

CROSS REFERENCE TO RELATED APPLICATIONS

This application is a divisional of U.S. application Ser. No. 13/028,893, filed Feb. 16, 2011 (currently published). U.S. application Ser. No. 13/028,893 is a continuation of U.S. application Ser. No. 12/886,264, filed Sep. 20, 2010 (abandoned). U.S. application Ser. No. 12/886,264 is a continuation of U.S. application Ser. No. 12/391,829, filed Sep. 4, 2009, now U.S. Pat. No. 7,798,646, issued Sep. 21, 2010. U.S. Pat. No. 7,798,646 is a divisional of U.S. application Ser. No. 10/571,230, filed Mar. 6, 2006, now U.S. Pat. No. 7,494,222, issued Feb. 24, 2009. U.S. Pat. No. 7,494,222 is a national stage application of international application no. PCT/US2004/29003, filed Sep. 3, 2004 (expired). International application no. PCT/US2004/29003 claims the benefit of U.S. Provisional Application No. 60/500,163, filed Sep. 4, 2003.

FIELD OF THE DISCLOSURE

The present disclosure relates to methods and apparatus for the diagnosis of impaired dark adaptation and/or the identification of individuals who are at-risk of disease states related to impaired dark adaptation.

BACKGROUND

The macula of the human eye, which is about 6 mm in diameter and covers the central 21.5 degrees of visual angle, is designed for detailed vision. The macula comprises a small cone-dominated fovea surrounded by a rod-dominated parafovea (Curcio 1990, J. Comp. Neurol. 292:497). Rods are responsible for vision in dim light while cones are responsive to bright light and colors. In young adults, the number of rods outnumbers cones by approximately 9:1. This proportion of rods to cones changes as individual's age. The health and function of the rod and cone photoreceptors are maintained by the retinal pigment epithelium (RPE), the Bruch's membrane and the choriocapillaris (collectively referred to as the RPE/Bruch's membrane complex). The RPE is a dedicated layer of nurse cells behind the neural retina. The RPE sustains photoreceptor health in a number of ways, including, but not limited to, maintaining proper ionic balance, transporting and filtering nutrients, providing retinoid intermediates to replenish photopigment bleached by light exposure and absorbing stray photons. The RPE and the photoreceptors are separated by the choriocapillaris, which provides blood flow to the neural retina. Further separating the RPE and the choriocapillaris is the Bruch's membrane, a delicate vessel wall only 2-6 μm thick.

As the function of the RPE/Bruch's membrane complex is impaired, the result is deficient nutrient and oxygen transport to the photoreceptors and reduced clearance of by-products of bleaching, such as opsin. Therefore, as a result of the impairments of the function of the RPE/Bruch's membrane complex, the health and function of the photoreceptors may be impaired. This is especially true with the rod photoreceptors, which are responsible for scotopic, or dark-adapted vision. The impairment of the rod photoreceptors may lead to impairment in dark adaptation. Dark adaptation is defined as the recovery of light sensitivity by the retina in the dark after exposure to a bright light. In this regard, dark adaptation can essentially be viewed as a bioassay of the health of the RPE, the Bruch's membrane and the choriocapillaris, and impaired dark adaptation may be used as a clinical marker of disease states that impair one or more of the RPE, the Bruch's membrane and the choriocapillaris. Such disease states include, but are not limited to age-related macular degeneration (ARMD; which is also known as age-related maculopathy ARM), vitamin A deficiency, Sorsby's Fundus Dystrophy, late autosomal dominant retinal degeneration, retinal impairment related to diabetes and diabetic retinopathy. Patients with ARMD often have impaired dark adaptation as a result of the pathophysiology associated with ARMD. Dark adaptation may be particularly useful in this regard since deficits in dark adaptation generally occur before clinical manifestations of the disease state become evident.

Currently ARMD is the leading cause of new, untreatable vision loss in the elderly populations of the industrialized world (Mitchell 1995, Ophthalmology, 102:1450; Vingerling 1995, Ophthalmology, 102:205). With the increasing proportion of old adults in industrialized countries, the impact of ARMD on health care costs will worsen (Council 1998, Vision Research—A National plan 1999-2003; Executive Summary). ARMD is a heterogeneous disorder and is related to the breakdown of one or more components of the RPE/Bruch's membrane complex. As discussed above, impairment of the RPE/Bruch's membrane complex can impact the health and functionality of the photoreceptors and lead to impaired dark adaptation.

Early to intermediate ARMD is characterized by minor to moderate vision loss associated with extracellular lesions, and changes in the RPE pigmentation and morphology. The lesions between the RPE and the Bruch's membrane can be either focal (referred to as drusen) or diffuse (referred to as basal linear deposits). Advanced ARMD is characterized by severe vision loss associated with extensive RPE atrophy with or without the squelea of choroidal neovascularization (which is the in-growth of choroidal vessels through the Bruch's membrane and under the RPE in the plane of the drusen and/or the basal linear deposits). In the United States late stage ARMD accounts for 22% of monocular blindness and 75% of legal blindness in adults over the age of 50 (Klein 1995, Opthamol. Vis. Sci. 36:182). It is currently believed that ARMD is a multi-factorial process involving a complex interplay of genetic and environmental factors. The principal treatment for late stage ARMD is photocoagulation of the aberrant blood vessels comprising the choroidal neovascularization. However, only a subset of patients with existing neovascularization will qualify for such treatment.

A potential treatment approach is to prevent or delay the onset of late stage ARMD. For example, the Age-related Eye Disease Study (2002) indicated that the intake of several anti-oxidant compounds (such as beta-carotene, vitamin C and vitamin E in conjunction with zinc and copper) was beneficial in preventing neovascularization in intermediate ARMD patients with drusen in both eyes, which places them at high risk for developing advanced ARMD (AREDS report no. 8, 2001). A number of therapeutics such as anecortave acetate (Retaane; Alcon Labs), pegaptabnib sodium (Macugen; Eyetech), ranibizumab (Lucentis; Genetech) and combretastatin (CA4P; Oxigene) are in various stages of development. Other treatment options under investigation range from brachytherapy to rheopheresis, and observational studies have been examining possible protective roles for anti-inflammatory and lipid-lowering drugs.

However, these approaches require that patients at risk for ARMD or other disease states that impact the RPE/Bruch's membrane complex and/or dark adaptation be identified early enough so that preventive measures can be undertaken. Furthermore, advising patients whether the risk and cost of a treatment is warranted requires the ability to monitor whether their disease progression is affected by their course of treatment. Such a diagnostic method suitable for widespread, clinical use is currently not available in the art. The present disclosure provides such a method to identify deficits in dark adaptation and describes an apparatus capable of carrying out said method. Such deficits in dark adaptation may be used to identify those at risk for developing disease states that impact the RPE/Bruch's membrane complex and/or dark adaptation and tracking the disease/treatment progression among those already affected by the disease.

DETAILED DESCRIPTION

Figure 1:
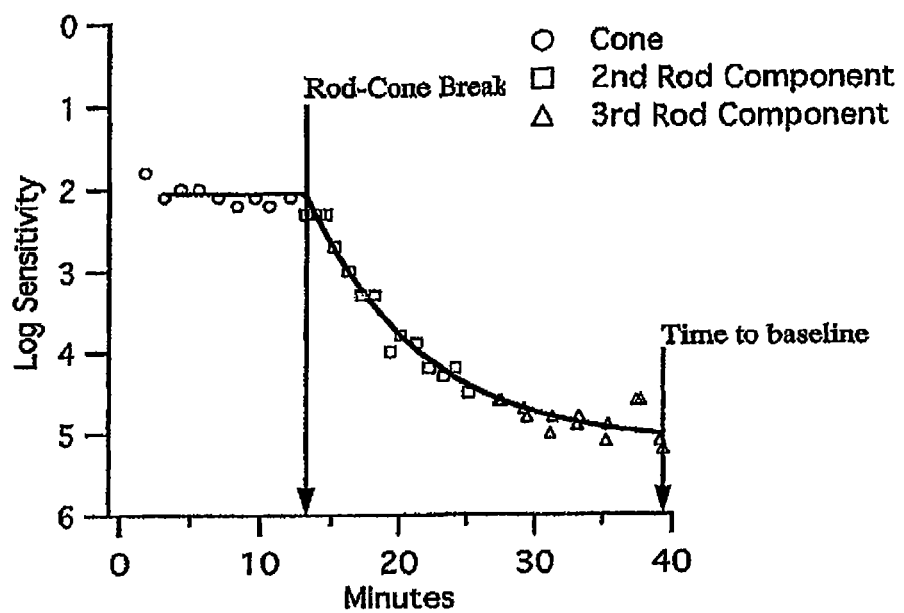
FIG. 1 is an exemplary dark adaptation curve illustrating the various components of dark adaptation.

The human macula comprises a small cone-dominated fovea surrounded by a rod-dominated parafovea. The function of the rod and cone photoreceptors is impacted by the health of the components of the RPE/Bruch's membrane complex. As the function of the RPE/Bruch's membrane complex is impaired, the result is deficient nutrient and oxygen transport to the photoreceptors and reduced clearance of by-products of bleaching, such as opsin. Therefore, as a result of the impairments of the function of the RPE/Bruch's membrane complex, the health and function of the photoreceptors may be impaired. In many cases, the rod photoreceptors are especially vulnerable. The rod photoreceptors are responsible for scotopic, or dark-adapted vision. The result of damage to the rod photoreceptors is impaired dark adaptation in the subject. Therefore, impaired dark adaptation can be a surrogate marker for damage to the RPE/Bruch's membrane complex and may be used to diagnose individuals with disease states that have their clinical manifestations via their impact on the RPE/Bruch's membrane complex and/or to identify those individuals who may be at risk for developing such disease states. Such disease states, include but are not limited to, ARMD, vitamin A deficiency, Sorsby's Fundus Dystrophy, late autosomal dominant retinal degeneration, retinal impairment related to diabetes and diabetic retinopathy. However, prior methods for determining impaired dark adaptation are cumbersome and time consuming to administer.

What the art is lacking is a method to determined impaired dark adaptation which is a sensitive and accurate indicator of those patients suffering impaired dark adaptation, which produces high test-retest reliability and reproducibility, which can be administered in the clinical setting with decreased burden on the subject and the healthcare provider, and which is simple to administer. The subjects identified with impaired dark adaptation can then be evaluated for a variety of disease states, such as, but not limited to, those discussed herein. For example, patients with impaired dark adaptation can be monitored for increased risk of ARMD. In addition, patients identified with ARMD can be monitored to track ARMD disease progression, such as but not limited to, the progression from early ARMD to intermediate ARMD or intermediate ARMD to advanced/late ARMD. Furthermore, such individuals may be started on early intervention strategies to prevent or delay the onset of ARMD and the effectiveness of such intervention strategies can be monitored.

The present disclosure describes a new method for the measurement of rod-mediated dark adaptation to prospectively identify subjects who have impaired dark adaptation and who are at-risk for developing a variety of disease states, such as ARMD, and which meets limitations imposed by the clinical setting. The method can be administered in a short time (in as little as 20 minutes or less) in the clinical setting. As a result, healthcare providers will be able to offer the test on a practical and affordable basis, making application of the test and realization of its benefits more widespread. In addition, the burden the test imposes on the subject and the healthcare provider will be significantly reduced. Importantly, the method and apparatus described allows a broader range of subjects to be tested, for instance children or those with impaired cognitive ability. Furthermore, the subject need not have prior exposure to psychophysical test methods. An apparatus for administering such a method is also described.

In addition to its use as a diagnostic tool, the method described herein can be used to identify the structural, biochemical and physiological changes responsible for the visual dysfunction associated with impaired dark adaptation and the progression of the disease states associated with impaired dark adaptation, such as, but not limited to, ARMD, vitamin A deficiency, Sorsby's Fundus Dystrophy, late autosomal dominant retinal degeneration, retinal impairment related to diabetes and diabetic retinopathy. This is particularly useful since many of such disease states are currently believed to be a heterogeneous rather than a unitary genetic phenomenon and thus may have a variety of clinical manifestations depending on the underlying cause. By the early and accurate identification of those individuals at risk for developing ARMD and the other disease states discussed herein (by virtue of their identification as having impaired dark adaptation) the structural, biochemical and physiological changes can be identified and correlated with various stages of disease state progression. Such information can be used to design theoretical models of the disease state, evaluate animal models of the disease state and to identify new opportunities for therapeutic intervention in the treatment of the disease state.

The present disclosure presents ARMD as an exemplary disease state to be studied using impairment of dark adaptation in a subject. However, the method of determining such dark adaptation is applicable to the other disease states discussed herein and in any disease state that impacts one or more components of the RPE/Bruch's membrane complex.

The present disclosure shows that rod-mediated vision is more severely affected than cone-mediated vision in individuals at-risk for incident ARMD and in early ARMD patients. In addition, the impairment of rod-mediated vision appears to precede the impairment of cone-mediated vision. This relationship is significant since the most debilitating vision impairment associated with ARMD is caused by the loss of cone photoreceptors. Therefore, by monitoring the health of the rod-photoreceptors, which as discussed above is also indicative of the health of the RPE/Bruch's membrane complex, those individuals suffering from or at-risk for ARMD, can be identified. This earlier detection will result in the initiation of preventive measure, increased monitoring and/or early initiation of treatment before cone-photoreceptors are impaired. As a result, the most significant aspect of ARMD-related vision impairment may be prevented or delayed.

Most ARMD patients exhibit more rod-mediated (scotopic) visual sensitivity loss than cone-mediated (photopic) visual sensitivity loss. Rod-mediated dark adaptation is especially susceptible to the effects of ARMD, as discussed in more detail below and many early ARMD patients exhibit abnormal dark adaptation in the absence of other vision function abnormalities such as reduced acuity, contrast sensitivity or visual sensitivity. Methods do exist for the diagnosis and detection of ARMD. However, these methods are insensitive in that they generally detect only visible lesions associated with early ARMD (which indicates later stages of disease progression), and are subject to a large degree of clinical judgment, resulting in a range of interpretations of the test results. Most of the tests are too sophisticated for the average healthcare provider to administer. In addition, the interpretation of the test results requires years of clinical experience and even then can be subject to substantial variation. Current test methods also place a significant burden on the patient and the healthcare provider. No suitable method is currently available for the detection of ARMD that overcomes these obstacles. Even if the currently available tests are administered, they still do not reliably identify patients at risk for ARMD.

As an example, fundus photography and grading can be used to detect ARMD. However, fundus photography is not capable of detecting microscopic lesions or the biological changes associated with ARMD. Anatomical and histopathological studies of donor eyes indicate that the pathological processes underlying ARMD, and the subsequent damage caused by these processes, are well underway before fundus photography can detect signs of ARMD. In addition, the test is relatively expensive, requires specialized equipment and training to administer and is subject to variations in interpretation. Reliable interpretation of fundus photographs is possible by utilizing a fundus reading center. However, the use of a fundus reading center for routine clinical use is impractical because of the cost and turn around time of the results, which generally takes several months. As a result, fundus photography has not been widely used as a means to diagnose ARMD. As an additional example, flourosceine angiography is currently used as the method of choice for diagnosing late state ARMD. However, this method is invasive as the flourosceine dye must be administered to the subject via the IV route. In addition, reactions to the flourosceine dye occur for approximately 1-1000 subjects. These reactions may be severe and may even be fatal in some cases. As a result, a physician is required to be in attendance during the procedure. Therefore, the burden on the subject and the healthcare professional is quite high.

General Description of Test Parameters

A general description of the method and the parameters involved in the method disclosed is given below. In the method described, dark adaptation is measured with a custom, computerized automated adaptometer. The subject undergoing testing is subject to a bleaching protocol. The bleaching protocol may be varied as is known in the art. The bleaching protocol adapts the test eye to a light of a first luminance level (by desensitizing a portion of the rhodopsin molecules in the test eye on exposure to the light of a first luminance level). Visual recovery (i.e. dark adaptation) is then measured as the test eye adapts to a light of a second luminance level. Therefore, the first luminance level serves as a standardized baseline from which visual recovery is measured. Any bleaching protocol that provides this standardized baseline may be used in the method and apparatus described herein. The first luminance level is brighter than the second luminance level, but the absolute intensity values of the first and second luminance levels may be varied as desired. Generally, the greater the absolute value of the first luminance level, the shorter the period of exposure of the test eye to the light of the first luminance level to achieve the baseline. For example, the light of the first luminance level may be an intense light, such as that provided by an electronic strobe or flash, and the light of the second luminance level may be at or close to 0 $cd/m^2$, such as would occur in a dark room. Alternatively, the light of the first luminance level may be a light produced by an ordinary light bulb or by the ambient light in a room, and the light of the second luminance level may be at or close to 0 $cd/m^2$, such as would occur in a dark room.

Many light delivery methods can be used to deliver the light of the first luminance level (which is referred to hereafter as a bleaching light), such as photographic flashes, adapting fields, illuminated backgrounds, direct projection into the eye, exposure to ambient light, or staring into a light bulb. As discussed above, there are numerous possibilities. Classically, subjects viewed an adapting field to bleach the photopigment. This bleaching method causes discomfort to the subject, and it is difficult to reliably deliver bleaches in psychophysically inexperienced subjects. Another method of bleaching is to project light into the eye using a Maxwellian view system. This method causes less irritation, but requires the subjects to fixate very steadily and not blink for 30 to 60 seconds. Many inexperienced subjects find this to be a difficult task. If the subject changes fixation or blinks, it is necessary to wait up to 2 hours before the bleach is repeated to avoid the cumulative effects of bleaching. Bleaching light delivered by an electronic strobe or flash delivers a high intensity light in a short period of time. Because the light exposure is brief and can be localized outside the fovea, it is not irritating to the subjects and the subjects do not need to maintain fixation for long period of time. With proper patient instructions blinking is not an issue.

The bleaching protocol desensitizes the desired amount of rhodopsin molecules and provides a standardized baseline to measure visual recovery to the second luminance level. The intensity of the bleaching light or the time of exposure to the bleaching light can be modulated to produce the desired amount of desensitization. In one embodiment, an equivalent of about 50% to 100% of the rhodopsin molecules is desensitized. The bleaching light may be an achromatic camera flash. The intensity of the bleaching light can be adjusted to desensitize the appropriate amount of rhodopsin molecules. For example, a bleaching light intensity of 7.48 log scot Td/sec will bleach approximately 98% of the rhodopsin molecules, while a bleaching light intensity of 5.36 log scot Td/sec will bleach approximately 50% of the rhodopsin molecules. Alternate bleaching light intensities which desensitize less than 50% or more than 50% of the rhodopsin molecules may also be used if desired.

After the bleaching protocol, visual recovery to the second luminance level is monitored. This recovery of light sensitivity is mediated primarily by the retina and measures predominately rod-mediated sensitivity. The subject provides a series of responses to the target stimulus (which is varied in intensity as described herein) which is used to generate one or more index factors. The index factors are used in a comparison step to determine a dark adaptation status of the subject. In one embodiment, the response of the subject is used to determine a threshold measurement. During threshold measurements, the subject is presented with a target stimulus. The target stimulus may be a spot of light, including a light spot on a darker background or a dark spot on a lighter background. Subjects may view the target stimulus with or without their best optical correction for the test distance. A variety of classical methods can be used to determine the threshold measurement, including but not limited to method of limits, just noticeable difference, and method of adjustment. These techniques are well known in the art. Thresholds measurements can be sampled in such a way as to provide sufficient data to fit models of dark adaptation. In one embodiment, threshold measurements are sampled once every 1 to 5 minutes. Another embodiment would be to sample threshold measurements twice every minute. Yet another embodiment would be to sample 2 threshold measurements per minute early during the test then sample 1 threshold measurement every 2 minutes thereafter. Higher or lower sampling rates may be used as desired to balance the need of producing an adequate dark adaptation function for model fitting against subject burden. As an example of lower sampling rates, a small number of threshold measurements may be sampled based on predictions of rod photoreceptor function in normal individuals. For example, a threshold measurement may be obtained at 3-5 minutes (which in a normal individuals would be before the rod-cone break) and at 5-10 minutes and 10-15 minutes. If these threshold measurements do not correlate with the rod photoreceptor function in normal individuals, the subject is likely to have impaired dark adaptation. Such a sampling schedule would further reduce subject burden.

In one embodiment, a modified staircase threshold procedure may be used to determine the threshold measurement. In one embodiment, a 3-down 1-up staircase procedure is utilized. The "3-down" refers to the decrease in intensity of the target stimulus, while the "1-up" refers to the increase in intensity of the target stimulus during selected portions of the threshold measurement. Variations in the decrease or increase in the intensity of the target stimulus may be used without altering the scope of the present disclosure. An example illustrating the use of a staircase procedure is given below as an example. In the staircase procedure, the initial target stimulus intensity starts out at a predetermined intensity. In one embodiment, the initial target stimulus intensity is 4.85 cd/m$^2$, although other initial intensities may be used. The target stimulus is presented at predetermined time intervals. In one embodiment the target stimulus is presented every 1-5 seconds, while in an alternate embodiment, target stimulus is presented every 2-3 seconds. The duration of the target stimulus presentation may also be varied. In one embodiment, the target stimulus duration is about 100 to 400 milliseconds, while in an alternate embodiment, the target stimulus duration is about 200 milliseconds. If the subject does not respond to the target stimulus, the target stimulus intensity remains at the initial intensity until the subject responds that the target stimulus is visible. If the subject indicates the target stimulus is visible, the target stimulus intensity is decreased by a predetermined amount until the subject stops responding that the target stimulus is present. For example, in a 3-down 1-up staircase, the target stimulus intensity is decreased by 3 "unit" increments, such as 0.3 log units, on successive measurements. After the subject responds that the target stimulus is invisible (by failure to respond to the presence of the target stimulus), the target stimulus intensity is increased by a predetermined amount until the subject responded that the target stimulus is once again visible. For example, in a 3-down 1-up staircase, the target stimulus intensity is increased by 1 "unit" increments, such as 0.1 log units, on successive measurements. This target stimulus intensity at which the subject reports the target stimulus is again visible is defined as the threshold and is recorded as the threshold measurement. The time and intensity level of the target stimulus are recorded (either manually or automatically by a means for control on the test apparatus). No threshold is recorded until the staircase is completed. Successive threshold measurements are initiated with a target stimulus intensity a predetermined amount brighter than the previous determined threshold measurement. For example, in a 3-down 1-up staircase, the target stimulus intensity is increased by 3 "unit" increments, such as 0.3 log units, for the next threshold measurement sequence. Alternatively, it is possible to use a traditional staircase technique in which only the reversals are recorded, or to record all of the subject responses to the target stimulus (i.e.; all raw data inputs used to obtain the thresholds). The subject responses are recorded as well as the time the response was determined. The subject responses may be used directly in the comparison step as discussed below. The subject responses may also be used to generate a plurality of threshold measurements as described herein, and said threshold measurements used in the comparison step as discussed below. The subject responses may be used in conjunction with an appropriate dark adaptation model (either with or without generating threshold measurements) to generate one or more of the index factors and said index factors used in the comparison step as discussed below. The subject responses or threshold measurements may be subject to certain noise reduction protocols to increase the quality of the threshold measurements and to eliminate artifacts that may be due to subject inattention or subject error. After processing for noise reduction, the responses or threshold measurements may be used as described. The noise reduction protocols may be applied as the responses or threshold measurements are generated, after all responses or measurements are acquired, or at any intermediate time point.

A variety of noise reduction protocols may be used. A preferred embodiment is non-destructive noise reduction, where outliers are deleted without altering the retained data. This approach has the advantage of preserving the absolute and relative information content of the threshold curve subject to noise reduction, as opposed to smoothing algorithms or transformation functions that alter the information content of the retained data. One such non-destructive noise reduction protocol is termed "threshold guidance". With threshold guidance, each threshold measurement obtained after the initial threshold measurement (referred to as a "presumptive threshold measurement") is compared to at least one preceding threshold measurement (referred to as the "base threshold measurement"). For example, the tenth threshold measurement obtained (the presumptive threshold measurement) may be compared with the ninth threshold measurement obtained (the base threshold measurement). Alternatively, the tenth threshold measurement obtained (the presumptive threshold measurement) may be compared to more than one preceding threshold measurement, such as the seventh through ninth threshold measurement (collectively, the base threshold measurement). Based on the physiological constraints of the adaptation of the retina between the first luminance level and the second luminance level and the time between the base threshold measurement and the presumptive threshold measurement, a maximum change in presumptive threshold measurement can be estimated accurately using the base threshold measurement. A range (referred to as the "window") is established given the maximum change possible and this range is applied to the base threshold measurement. The presumptive threshold measurement is then examined to determine if the presumptive threshold measurement falls with the established window. If the presumptive threshold measurement falls within the window, the presumptive threshold measurement is considered a valid threshold measurement and can be used as described. If the presumptive threshold measurement falls outside the window, the threshold measurement is considered invalid and is not considered further. In an alternate embodiment of threshold guidance, each presumptive threshold measurement is compared to a model fit of all or a portion of the base threshold measurement to determine whether the presumptive threshold measurement falls within an established window anchored to the model fit. For any embodiment of threshold guidance, the process may be automated by creating an algorithm that captures the desired criteria and applying the algorithm to the threshold measurements. Such an algorithm may be applied by the means for control as described herein. The threshold guidance technique may be applied as the threshold measurements are acquired or may be applied after all or a portion of the threshold measurements are acquired.

Another non-destructive noise reduction strategy is termed "curve guidance". In curve guidance, the threshold measurements are filtered using a statistical function of a defined width anchored to the threshold measurements or a model fit of the threshold measurements. Any threshold measurement that falls outside of the defined width is rejected and removed from further consideration. The filter can then be reapplied to the threshold measurements (either with the initial width or a modified width). Again, any threshold measurement that falls outside of the width is rejected and removed from further consideration. This process can be repeated as desired in an iterative manner to further refine the threshold measurements. In one preferred embodiment, the statistical function is a band pass filter or its equivalent having a width defined by a first statistical parameter of the threshold function and anchored to a moving means function of the threshold measurements. Other means of defining the filter width, such as cut points, limit functions or windows can be used. Other functions of the threshold measurements, such as autoregressions and weighted moving averages, can be used as the anchor. In another embodiment, the statistical function defining the filter width can be anchored to a model fit of dark adaptation applied to the threshold measurements.

Such noise reduction strategies will allow the unbiased examination of threshold measurements to determine their validity. As a result, invalid threshold measurements caused by subject error or inattention can be removed before the threshold measurements are applied to the appropriate dark adaptation model. This will widen the scope of subjects who can are eligible to undergo the described method and increase the reliability and reproducibility of the method described. The noise reduction strategies described may be applied alone or in combination.

The target stimulus is of a spectrum of light that is effective in isolating the rod response (i.e., stimulating the rods with no or little stimulation of the cones). A range of target stimulus wavelengths can be used to isolate the rod response. In one embodiment, the spectrum is comprised of at least one wavelength in the range from 400 nm to 550 nm. In an alternate embodiment, the spectrum is comprised of at least one wavelength in the range from 400 nm to 500 nm. In yet another alternate embodiment, the spectrum has a single wavelength of 500 nm. (a wavelength of light near the peak of rod photoreceptor sensitivity). The target stimulus may cover about 1.5 to 7.0 degrees visual angle. In one embodiment, the target stimulus covers about 2.0 to 3.0 degrees of visual angle. In yet another alternate embodiment, the target stimulus covers about 2 degrees of visual angle. As the size of the target stimulus increases to cover a wider degree of visual angle, the sensitivity of the test may decrease, but such increased target stimulus sizes may be used if desired. The target stimulus may be presented at a variety of locations, so long as the target stimulus is placed in an area where rod photoreceptors dominate. In one embodiment the target stimulus is presented at a location from 20 degrees in the inferior visual field on the vertical meridian to 2 degrees in the inferior vertical field on the meridian. In another embodiment, the target stimulus is located in the macula. In an alternate embodiment, the target stimulus is located adjacent to the macula. In yet another alternate embodiment, the target stimulus is located in an area of the macula that is not on or overlapping the fovea, such as the parafovea. Positioning the target stimulus on or overlapping the fovea may decrease the sensitivity of the method, but such locations may be used if desired.

The threshold measurements may be used to generate a full or a partial dark adaptation threshold function/curve. In such a threshold function/curve, one or more threshold measurements (which indicate sensitivity of recovery) are plotted as a function of time to generate the dark adaptation function/curve. Various scales for the sensitivity measurement may be used, such as a semi-log unit scale. The curve is not required to be generated, but may be helpful as a visual tool to aid the healthcare provider.

The obtaining of thresholds measurements may be terminated based on a decision rule. A number of decision rules are possible. For example, threshold measurements may be terminated after defined period of time has elapsed, when the subject's visual sensitivity ceases to change over a defined period of time or when the subject's sensitivity returns to a previously obtained baseline value measured prior to bleaching. Additionally, threshold measurements may be terminated if a specific dark index factor, such as a adaptation parameter, does not appear within a defined period of time (for example, if the rod-cone break or the rod intercept does not appear within said defined period of time), on the inability to fit the threshold measurements to an appropriate model of dark adaptation, or on the failure to make a sufficiently close match to the comparative database (discussed below).

The threshold measurements obtained as discussed above may be directly compared to the comparative database or may be applied to an appropriate dark adaptation model as discussed below. A variety of models may be used. These include models with one component or more than one component. Examples of models that may used include, but are not limited to, a one-linear, one-exponential model, a bi-linear model, and a tri-linear model. In one example of a two-component model, one component models the cone photoreceptors and one component models the rod photoreceptors. When more than two components are used in the model, the rods or the cones may be analyzed by the additional components of the model. However, it is more common for the rods to be analyzed by the additional components. In such a model, the cone photoreceptors, and the second and third rod components may all be analyzed with a linear function (a tri-linear model). The various components may use linear or exponential functions and may be fit using nonlinear regression or a least squares fit. Other statistical methods may also be used. Dark adaptation parameters, individual threshold measurements or other data may be extracted from the modeled data without providing a graphical threshold curve. Key dark adaptation function parameters that can be extracted from the model fit include, but are not limited to, the rod-cone break time, the rod intercept and the rod recovery time constant.

Figure 2:
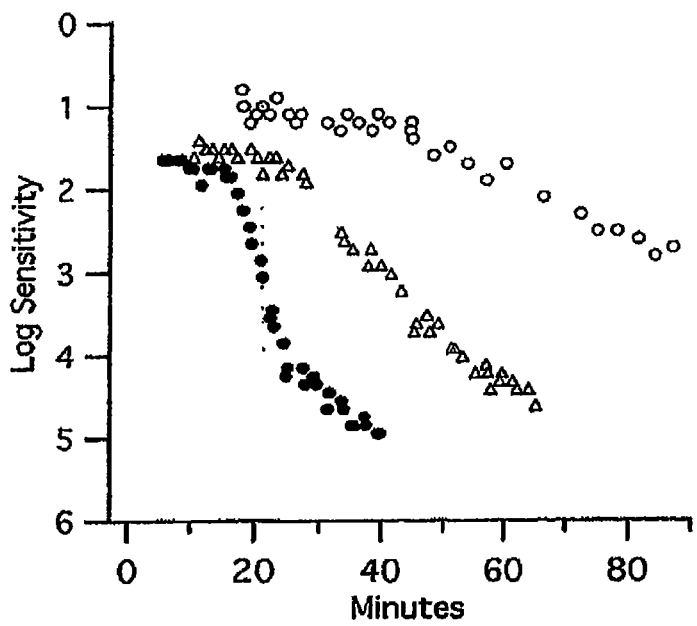
FIG. 2 compares exemplary dark adaptation curves for a normal old adult (closed circles), an early-stage ARMD patient (open triangles) and a late-stage ARMD patient (open circles).

In one preferred embodiment of a two component model, a linear function is used to analyze the cone photoreceptors while an exponential function is used to analyze the rod photoreceptors. In this model the linear component represents the rapid, cone-mediated portion of the recovery and the exponential recovery represents the slower, rod-mediated portion of the recovery. The point that connects these two components is defined as the rod-cone break, a parameter of interest in determining dark adaptation. The time constant of the exponential component is defined as the rod time constant, an additional parameter of interest. Other parameters may be analyzed as discussed below. This model has been shown to objectively estimate the rod-cone break and the time constant of rod sensitivity recovery. While it is known that the exponential rod-mediated recovery is actually comprised of second and third rod components, more detailed modeling does not necessarily result in improved analysis of dark adaptation. However, the second and third rod components may be analyzed by their own modeling components if desired. For some patients with late ARMD, this two-component model may not provide a satisfactory fit because insufficient sensitivity recovery after the rod-cone break will cause the exponential portion of the model to fit poorly. For example, FIG. 2 shows a comparison of dark adaptation curves generated by the method disclosed from a normal subject (closed circles), an early ARMD patient (open triangles) and a late ARMD patient (open circles). As can be seen, the rod mediated component of the curve generated from the late ARMD patient using the one-linear, one-exponential function would not provide a clear determination of the rod-cone break. For cases such as these where the two-component model proves inadequate ($R^2<0.9$), a bilinear model may be applied to the data to accurately estimate rod-cone break, and the other parameters of interest. The flexibility of employing multiple models will allow tracking of disease progression further than strict adherence to a single model.

The threshold measurements may be applied to an appropriate model fit as the threshold measurements are generated, after all threshold measurements are obtained or after a determined number of threshold measurements are obtained. For example, every time a valid threshold measurement is obtained, the threshold measurements may be applied to an appropriate dark adaptation model to determine if a threshold model fit can be achieved. Using this approach, the model may be generated instantaneously as the test progresses. In addition, if a model fit is not achieved in a predetermined amount of time (such as 5-10 minutes, the time point at which the rod-cone break should appear in a healthy individual), the threshold measurements may be terminated and the subject considered to have impaired dark adaptation. Alternatively, all threshold measurements may be obtained before the threshold measurements are applied to an appropriate model.

From the threshold measurements and the data generated during the modeling step, an "index factor" may be extracted. The index factor may be a threshold curve generated by the appropriate model from the threshold measurements, a partial threshold curve generated by the appropriate model from the threshold measurements, individual threshold measurements selected from the appropriate model, individual threshold measurements selected prior to modeling, a dark adaptation parameter determined from the appropriate model, or any combination of the foregoing. One or more index factors may then be compared with corresponding index factors determined from healthy individuals to determine the dark adaptation status of the subject.

The dark adaptation parameters include, but are not limited to, the time constant of the cone-mediated sensitivity recovery, the time constant of rod-mediated sensitivity recovery, the cone plateau, the rod plateau, the rod-cone break, the rod intercept, the slope and/or time constant of the $2^{nd}$ component of the rod-mediated recovery, the slope and/or time constant of the $3^{rd}$ component of the rod-mediated recovery, the transition time between the second and third rod-mediated components, and the duration from the bleaching to the final threshold measurement.

Figure 3:
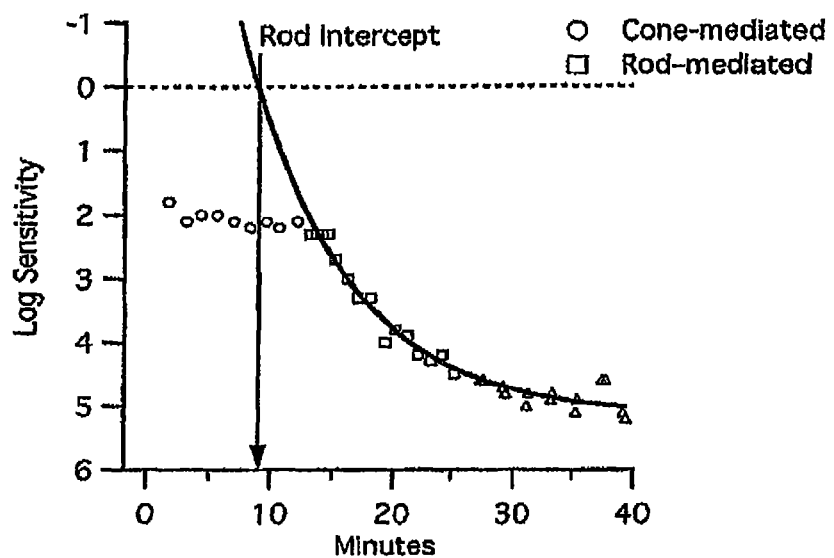
FIG. 3 is an illustration of the determination of the rod intercept dark adaptation parameter.

The dark adaptation parameters above are, with the exception of the rod intercept, described and known in the art and have the meanings known to one of ordinary skill in the art. The rod intercept is a novel parameter. In any test of dark adaptation, the cone photoreceptors contribute to the recovery of dark adaptation. While the rod-cone break is a sensitive indicator of dark adaptation impairment, the rod-cone break is dependent, in part, on cone photoreceptor function. The contribution of the cone photoreceptors is not uniform between individuals and impacts the timing of the rod-cone break. The contribution of the cone photoreceptors may also change over time, which may impact the data obtained over a period of time, such as might occur when monitoring a subject. It would be desirable to eliminate the contribution of the cone photoreceptors (which may be referred to as cone contamination) to the dark adaptation parameters. The rod intercept addresses this need. The rod intercept is the time at which the rod function would recover to (or "intercept") a reference sensitivity level in the absence of any cone function. Once the rod component of dark adaptation has been isolated or identified, an exponential model is fitted to the component. The rod intercept parameter is the time at which the exponential crosses the reference sensitivity value. The sensitivity value can be any value, but is most useful when the value is greater than the cone plateau. For purposes of example, the reference sensitivity level may be the zero sensitivity level, as this sensitivity level is above the cone plateau in all individuals. The rod intercept parameter is completely independent of the health and function of the cone photoreceptors and ideal for tracking the progression of dark adaptation impairment of the rods. An example of the rod intercept and its method of determination are given in FIG. 3. In this manner, the use of the rod intercept eliminates a confounding factor contributed by cone photoreceptor function and improves the sensitivity and specificity of the diagnosis of impaired dark adaptation.

The individuals in the comparative database may be aged matched to the subject, or may be non-aged matched as compared to the subject. For example, if the subject is 65 years of age, in one embodiment the comparative database may be composed of individuals with ages from 60 to 70 years, or in a second embodiment, the comparative database may be composed of individuals with ages from 25 to 40 years. The use of a comparative database comprising a younger population may offer certain advantages since the younger subjects that comprise the population will be more likely to be free of disease states and other conditions that may impact their dark adaptation. As discussed above, most prior techniques for diagnosing individuals with ARMD and other disease states are not sensitive enough to detect individuals with early stages of the disease states that can impact dark mediated adaptation. Therefore, using an age matched population for the comparison may actually decrease the sensitivity of the method to identify impairments in dark mediated adaptation since the age matched population of the comparative database may in fact have a certain degree of impaired dark adaptation.

The individuals making up the comparative database may be healthy (i.e., disease free) or they may be selected based on their diagnosis with ARMD or any of the other disease states which have impaired dark adaptation as a clinical manifestation, or both. If healthy individuals are selected, the index factors determined from the subject can be compared with the corresponding index factors for the healthy individuals. If individuals with a diagnosed disease state are selected, the index factors determined from the subject can be compared with the corresponding index factors for the individuals diagnosed with a disease states and/or defined stages of a disease state. In this manner, the comparison may be able to predict if the subject has impaired dark adaptation (from a comparison with healthy individuals in the comparative database), is suffering from a disease state (from a comparison with individuals in the comparative database diagnosed with said disease state) or to diagnose the severity of the disease state (from a comparison with individuals in the comparative database diagnosed with said stage of the disease state). For example, if the disease state is ARMD, the index factors determined for the subject may be compared to corresponding index factors from individuals in the comparative database who are diagnosed with early, intermediate or late stage ARMD. The stratification of the database, as discussed below, may aid in making such comparisons.

The comparative database may be stratified based on a number of stratification criteria. These criteria may be dark adaptation status, risk factors, demographic factors, other relevant factors or a combination of the preceding. Examples, of risk factors include, but are not limited to, age, smoking status, body mass index, and status with regard to health conditions (for example diabetes and ARMD status). Other risk factors may also be included. Demographic factors include, but are not limited to, lens density, gender and ethnicity. The inclusion of a specific stratification criteria as a risk factor or demographic factor may be modified (for example, age may be considered both a risk factor and a demographic factor). The individuals in the comparative database may be tagged or otherwise identified, such that the appropriate population of individuals in the comparative database may be selected for the comparison to the subject.

Furthermore, the comparative database may be refined over time. The individuals in the database may be followed over time and their health status monitored. If an individual no longer meets an inclusion criterion for the comparative database, the individual may be removed. The inclusion criteria may be development of a disease state or impaired dark adaptation within a defined time period of the inclusion of the individual in said comparative database. As one example, if an individual who was diagnosed as healthy and included in the comparative database as such develops a disease state or develops impaired dark adaptation within a time period (for example 5 years of their inclusion), the individual may be removed from the comparative database since it is possible that the data obtained from said individual may be tainted by early clinical manifestations of the disease state or impaired dark adaptation. In this manner the quality of the comparative database may be improved over time, resulting in a database with improved sensitivity and specificity.

One or more of these index factors is then compared to the corresponding index factors obtained from appropriately selected individuals in a comparative database. Appropriately selected means that the index factor from a defined group of individuals in the comparative database is selected for comparison to the index factor from the subject. The defined group may be all the individuals in the database or less than all the individuals in the comparative database. The defined group may be selected on the basis of stratification criteria as discussed above. The healthcare provider may select the defined group, with such selection based on one or more defining characteristics of the subject. For example, if the subject is a 60 year old, non-smoking, Caucasian male suspected of having ARMD, the stratification criteria may be used to select the defined group from the comparative database for the comparison step. In one embodiment, the defined group may be selected on the basis of ethnicity (Caucasian), gender (male), health status (disease free or diagnosed with ARMD), and age (20-45 years of age). Furthermore, the comparison may be carried out multiple times for any given subject to various iterations of the comparative database. For example, given the same 60 year old, non-smoking, Caucasian male subject suspected of having ARMD, a second comparison could be made using a defined group from the database selected on the basis of gender (male) only, or selected to include all individuals in the comparative database.

The comparison may be made to the absolute value of the appropriate index factor or to a normal reference range of the appropriate index factor from the comparative database to determine a dark adaptation status of the subject. The normal reference range is a statistical range about said index factor. In one embodiment, the statistical range is the mean of the values for the selected index factor from the comparative database ±two standard deviations of the mean; other statistical ranges may also be used. If the index factor determined for the subject satisfies an "impairment criteria" the subjects is considered to have an impaired dark adaptation status. If the index factor determined for the subject does not satisfy an "impairment criteria" the subjects is not considered to have an impaired dark adaptation status.

The impairment criteria may vary depending on the nature of the defined group selected from the comparative database for the comparison step. If a comparison is made to a defined group of healthy individuals from the comparative database, the impairment criteria is satisfied if one or more of the index factors determined for the subject fall outside of the normal reference range for the corresponding index factors in the comparative database. In this case, the subject is considered to have an impaired dark adaptation status and to be at risk for ARMD and the other disease states described herein. If a comparison is made to individuals from the comparative database having a diagnosed disease state and/or a specific stage of a disease state, the impairment criteria is satisfied if one or more of the index factors determined for the subject fall within the normal reference range for the corresponding index factors in the comparative database. Again, the subject is considered to have impaired dark adaptation and to be at risk for ARMD and the other disease states described herein.

In addition, the method disclosed may incorporate certain "compensation strategies". These compensation strategies may be used to account for variations in lens density, pupil size and other confounding factors that may impact the results of the method. For example, increased lens density may impact the results of the method since as lens density increases, less light passes through the lens to impact the photoreceptors. One method to account for this factor is to determine the lens density prior to implementing the method. One method of determining lens density is laser inferometry. The lens is scanned with a laser as is known in the art and a determination of lens density is made. This determination may be used to adjust the data prior to the analysis or may be used to adjust one or more parameters of the method prior to implementing the method, such as the intensity of the bleaching light and the intensity of the target stimulus. In this manner, the parameters may be adjusted so as to provide the same intensity of bleaching light and target stimulus to the photoreceptors of subjects with altered lens density as to those subjects with normal lens density. As another example, pupil size may also impact the results of the method. The pupils may be dilated prior to implementation of the method so as to provide a standardized baseline for the test. Alternatively, the dilation step may be omitted and a mask or artificial pupil may be used to allow the bleaching light and target stimulus to interact with a standardized portion of the pupil.

Reference Test Method

An embodiment of the general test methodology will now be described. The method described in this section was used to generate the data described in the Examples section below and the specification should not be construed as limited to the embodiment described below.

The target stimulus, in this case a spot of light, was presented to the subject as a 500-nm, circular spot of light covering 1.7 degrees of visual angle. The target stimulus was presented at 12° in the inferior visual field on the vertical meridian, which is adjacent to the macula. The test eye was subject to a bleach (0.25 ms in duration) using an electronic flash of achromatic light that produced a measured intensity of 7.65 log scotopic Trolands-sec, equivalent to inactivating ~98% of rhodopsin molecules in the test eye.

Threshold measurements were obtained immediately after flash offset. The control means on the test apparatus controls the psychophysical procedure and the parameters of the various steps and records the subject's responses. In this embodiment, a 3-down 1-up modified staircase threshold procedure was used to determine the threshold measurement. The initial target stimulus intensity was 4.85 cd/m$^2$ and the target stimulus was presented at 2-3 second time intervals for 200 milliseconds duration. If the subject did not respond to the target stimulus (indicating the target stimulus was visible), the target stimulus intensity remained at 4.85 cd/m$^2$ until the subject responded. If the subject indicated the target stimulus was visible, the target stimulus intensity was decreased by 0.3 log unit steps on successive threshold measurements until the subject stopped responding that the target stimulus was present. After the subject responded that the target stimulus was invisible (by failure to respond to the presence of the target stimulus), the target stimulus intensity was increased by 0.1 log units until the subject responded that the target stimulus was once again visible. This target stimulus intensity was defined as the threshold and the threshold measurement was recorded. No threshold was recorded until the staircase was completed. Successive threshold measurements were initiated with a target stimulus intensity 0.3 log units brighter than the previous determined threshold measurement. Successive threshold measurements were obtained as described above. Threshold estimates were obtained twice every minute for the first 25 minutes and twice every 2 minutes thereafter until termination. Threshold measurements were terminated when the subject's threshold measurements (which are an indication of rod sensitivity) were within 0.3 log units of the subject's previously measured baseline sensitivity.

To interpret the dark adaptation data (i.e., the threshold measurements), the thresholds were expressed as log sensitivity as a function of time (minutes) after the bleaching. Each subject's rod-mediated function was fit using a non-linear regression technique with a one-exponential, two-linear component model (McGwin, and Jackson 1999, *Behavior Research Methods, Instruments, and Computers* 31: 712). In this embodiment, the index factors were the dark adaptation parameters described above. One or more of these dark adaptation parameters was then compared to the reference ranges of the corresponding dark adaptation parameters obtained from an appropriately selected population of healthy subjects in a comparative database. From this comparison, a determination was made whether the subject's rod mediated dark adaptation process was impaired (i.e.; outside the reference range). A determination that a subject's rod-mediated dark adaptation was impaired suggests that the individual is at-risk for ARMD or is suffering from ARMD.

The decision rule for determining whether a dark adaptation parameter is abnormal was based on comparison of the subject's dark adaptation parameter(s) to corresponding dark adaptation parameters in a well-defined comparative database. In the Examples below, the comparative database was composed of adults of normal retinal health in the age range of 20 years old to 45 years old. The comparison was made to the reference range of the comparative database for the selected dark adaptation parameter. The reference range was the mean of the values for the selected dark adaptation parameter from the comparative database ±two standard deviations of the mean. If the subject's dark adaptation parameter fell outside the reference range for the corresponding dark adaptation parameter from the comparative database, dark adaptation is considered impaired and the subject is considered to be at-risk for ARMD. If several dark adaptation parameters were estimated, and any one the subject's determined dark adaptation parameters fell outside the reference range for the corresponding dark adaptation parameter from the comparative database for any single parameter, dark adaptation is considered impaired and the subject is considered to be at-risk for ARMD.

Optimization of Test Parameters

As previously discussed, one drawback to the current methods for analyzing dark adaptation impairment is the length of times the current methods require. Current methodologies may require 90 minutes or more for completion. Using the methods of the current disclosure, determination of dark adaptation impairment may be determined in less than 20 minutes. At least two variables influence the time taken to analyze dark adaptation impairment: 1) the intensity of the bleaching light; 2) and the location at which the target stimulus is presented. The lower the bleaching light intensity, the faster scotopic sensitivity will recover. Similarly, moving the location at which the target stimulus is presented into the macula from just outside the macula will shorten the time to recovery in normal patients.

Previous studies indicated that weaker bleaching protocols may provide less sensitive results for dark adaptation studies. However, surprisingly, a weaker bleaching protocol using a desensitizing flash of 5.36 log scot Td/sec decreased the time required to determine the rod-cone break and increased the ability to discriminate between early ARMD subjects and normal adults. In one study, dark adaptation curves were generated from an early ARMD subject and a subject with normal retinal health (using the reference test method described above) using identical parameters, with the exception that the intensity of the bleaching flash was varied between 7.48 log scot Td/sec (high intensity bleaching procedure, inactivating approximately 98% of the rhodopsin molecules) and 5.36 log scot Td/sec (low intensity bleaching procedure, inactivating approximately 50% of the rhodopsin molecules). Dark adaptation curves were generated as described herein and the rod-cone break and rod time constant dark adaptation parameters were analyzed for each patient under each condition. The results of the study are shown in Table 1 and FIG. 4.

Figure 4:
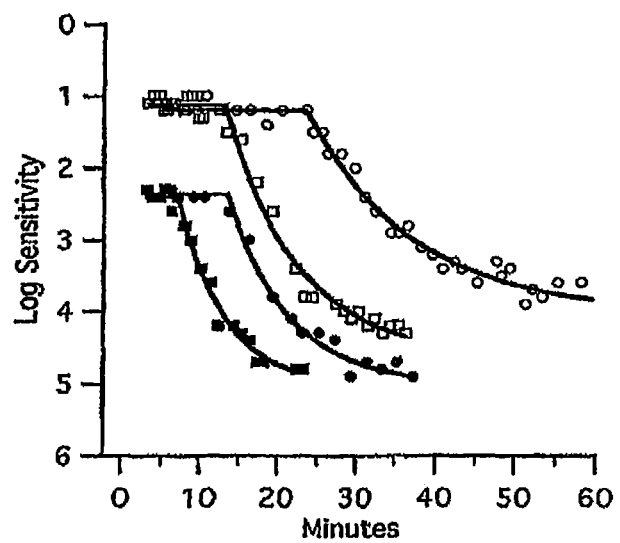
FIG. 4 shows the results of varying the intensity of the bleaching light from a high intensity (open circles and squares) to a low intensity (closed circles and squares) on dark adaptation curves.

Table 1 shows that the time to the rod-cone break was shortened by more than 8 minutes for both the normal subject and the early ARMD subject (to under 14 minutes in both cases). For the normal subject, the time to reach the rod-cone break using the high intensity bleaching protocol was 15.41 minutes, while the time to reach the rod-cone break in the early ARMD subject was 23.42 minutes. Using the low intensity bleaching procedure, the times were reduced to 7.15 minutes and 13.56 minutes, respectively. Despite the decreased timescale to determine the rod-cone break parameter, the ability to discriminate between those with early ARMD and normal subjects was increased using the low intensity bleaching procedure. As shown in table 1, using the high intensity bleaching procedure the early ARMD patient showed a 52% impairment. In contrast, when the low intensity bleaching procedure was used, the early ARMD patient showed a 90% impairment. Furthermore, the subjects exhibited well defined dark adaptation functions in response to the low intensity bleaching procedure. Such well defined dark adaptation functions with a prominent rod-cone break parameter aid in the analysis of the data and enhance repeatability and ease of use. FIG. 4 shows that the dark adaptation curves generated using the different bleaching parameters. In FIG. 4, the squares represent a 66-year-old normal adult while the circles represent a 79-year-old ARMD patient. The closed circles and square indicate the low intensity bleaching procedure was used, while the open circles and squares indicate the high intensity bleaching protocol was used. As can be seen, the low intensity bleaching procedure resulted in a quicker dark adaptation response, which as discussed above, actually increased the sensitivity of the discrimination between those subjects with early ARMD and those subjects with normal retinal health.

The impact of changing the location at which the target stimulus is presented was also evaluated. The standard research protocol described above tests dark adaptation with the target stimulus presented at 12° in the inferior visual field on the vertical meridian, corresponding to a peripheral location just adjacent to the macula. Because ARMD-related impairment of the rod photoreceptors is greatest near the fovea and decreases as a function of eccentricity towards the peripheral retina, testing dark adaptation at a more central location within the fovea should exhibit greater impairment than at a peripheral location. Dark adaptation curves were measured for a cohort of 10 ARMD patients (mean 73 years old) and a cohort of 11 normal old adults (mean 70 years old). Each subject's dark adaptation was measured twice: once using a target stimulus presented at 12° on the inferior vertical meridian and one using a target stimulus presented at 5° on the inferior vertical meridian. All other test parameters were unchanged from the reference method described above. The two measurements were counterbalanced and conducted on separate days to avoid practice effects or carryover effects. Several dark adaptation parameters generated from the dark adaptation curves using the two-component dark adaptation model are listed in Table 2.

As can be seen in Table 2, the times to rod-cone break changed in opposite directions for the two cohorts. It decreased (as expected) by 0.78 minutes for the normal old adults, but increased by 3.55 minutes for the ARMD patients. These opposing shifts further increased the ability to discriminate ARMD patients from normal old adults. Specifically, the ARMD cohort showed a 31% dark adaptation impairment relative to the normal old adults when the target stimulus was presented at 12° on the inferior vertical meridian (20.48 minute rod-cone break vs. 15.61 minutes for normal old adults), but the impairment increased to 62% when the target stimulus was presented at the more central 5° inferior field location (20.48 minute rod-cone break vs. 15.61 minutes for the normal old adults).

These modifications may be incorporated into the method described above to further decrease the time to implement the method and to further increase the ability of the method to discriminate between patients with impaired dark adaptation and those patients with normal dark adaptation.

General Description of Test Apparatus

The exact form and nature of the apparatus for conducting the method described herein may vary, as would be known to one of ordinary skill in the art. An exemplary arrangement of an apparatus capable of applying the method described herein is provided below. The apparatus may be modified and altered as would be obvious to one of ordinary skill in the art without deviating from the teachings disclosed herein.

In its most basic form, the apparatus comprises a means for generating a target stimulus, means for displaying a target stimulus (which is used to measure the recovery of visual sensitivity) and a means for input to allow the subject to convey to the healthcare provider information regarding the target stimulus (such as that the target stimulus is visible or the target stimulus is not visible). Other functions may be incorporated into the apparatus, such as a means for bleaching the test eye, a means for aligning the test eye, a means for confirming alignment and similar items. In one embodiment, the means for displaying may be an optical system. In such embodiment, a light source produces a light that is acted on by one or more optical elements to produce the target stimulus and project the target stimulus onto a screen or other display or through a diffuser for visualization by the subject. In an alternate embodiment, the means for displaying may be an electronic system. In such embodiment, the target stimulus is produced by an electronic means and is displayed on a CRT display, a liquid crystal display, a plasma display or an LED display for visualization by the subject. Each of these embodiments is described below.

In the embodiment where the means for generating is an optical system, the optical system comprises the elements to generate and act on the target stimulus such that the target stimulus has the desired characteristics. The means for generating comprises at least one of a light source, one or more optical elements and a screen or other display. The light source will be used to generate a light beam which will become the target stimulus, referred to as the target spot. There may be multiple or single light sources to generate the light beam. In one embodiment, the light source is a bank of light emitting-diodes (LEDs). The light source may also be a tungsten lamp or any other appropriate light source. The light source may emit white light and the light beam (in this case white light) produced may be acted upon by various optical elements to produce a light beam of a desired spectrum, or there may be multiple light sources to generate light of various wavelengths directly such that the light beam has a particular spectrum of wavelengths determined by the light emitted from the selected light source. Such light sources could be placed on a means for rotation so that the appropriate light source could be selected as desired.

The light beam generated by the light source may be acted upon by a series of optical elements to produce the target spot. A variety of optical elements may be used in various combinations to determine the properties of the light beam. These include directing means to direct the light beam, refining means to collimate and shape the light beam, selecting means to select the desired spectrum of the light beam, and modulating means to control the intensity of the light beam. In one embodiment, the directing means are mirrors, the refining means is shaping optics, the selecting means is an optical filter, and the modulating means is a neutral density filter or an electronic modulator. Additional optical elements may also be incorporated, such as an optical splitter to direct a portion of the light beam to a calibration detector to record the characteristics of the light beam and to ensure the characteristics of the light beam are as desired. The target spot is then directed to a means for display, which may be a screen or other visual display.

In the alternative, the means for generating may be electronic in nature. The target stimulus may be generated by electronic rather than optical means as described above. In this embodiment the target stimulus is generated electronically. The electronics produce the appropriate wavelength of light for the target stimulus. Alternatively, a filter may be inserted over the CRT display, the liquid crystal display, the plasma display or an LED display, or other appropriate display to impart to the target stimulus the appropriate wavelength. The target stimulus is then displayed on a means for display, which may be a CRT or LED screen, or other appropriate display.

The apparatus may be portable or fixed in a permanent location. In one embodiment, the subject may be confined in a testing booth and the apparatus may be a part of the testing booth or placed in the testing booth. The healthcare provider, may be located outside the testing booth to supervise the operation of the apparatus. An advantage of this embodiment is that the healthcare provider will be in normal light during the implementation of the method and can better monitor the method.

Exemplary Test Apparatus

Figure 5A:
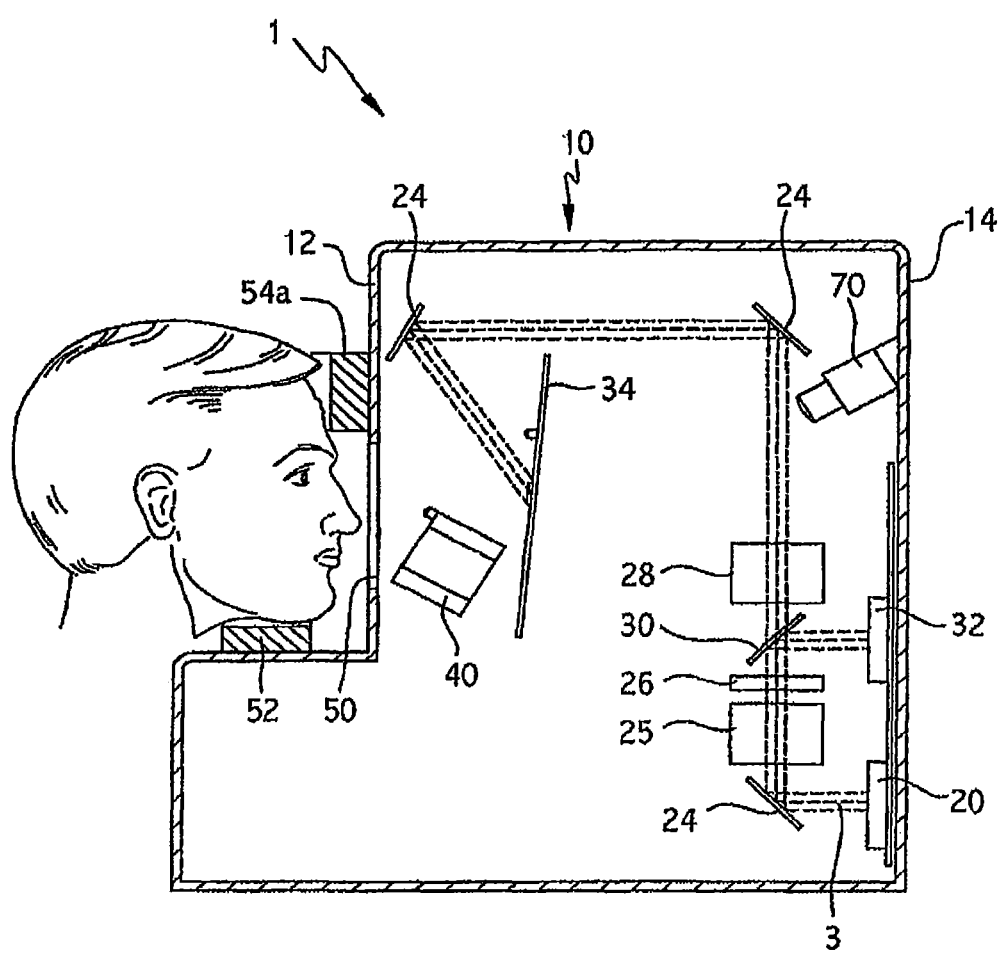
FIG. 5A shows a schematic of one embodiment of the apparatus of the present disclosure
Figure 5B:
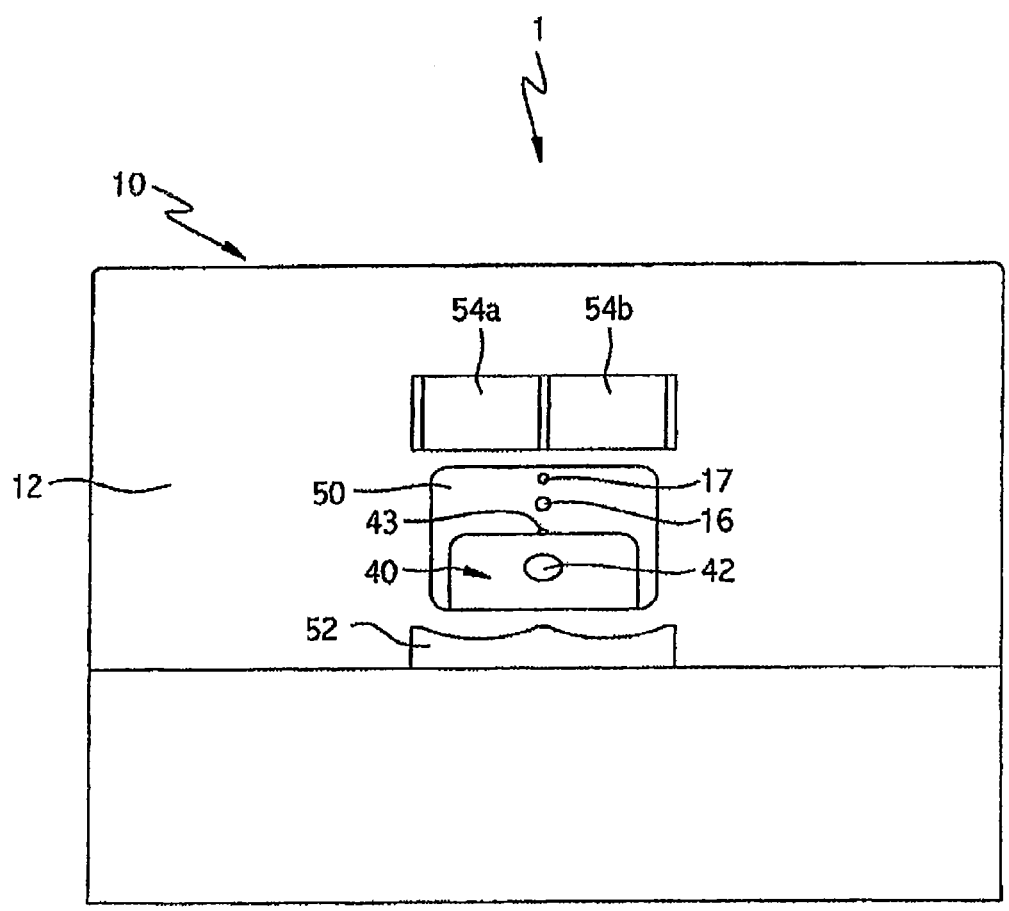
FIG. 5B shows a schematic of one embodiment of the interior of the apparatus of the present disclosure as viewed by a subject.

One embodiment of the apparatus is shown in FIGS. 5A and 5B. This embodiment illustrates the means for generating as an optical system. The apparatus 1 comprises a housing 10 having a front side 12 and a rear side 14 joined by side walls and bottom and top walls. The housing 10 has a viewing opening 50 to receive the head of the subject and allow the subject to view the display means, such as screen 34. The viewing opening 50 may be adapted to eliminate or reduce ambient light from entering the viewing opening and apparatus. The housing 10 is adapted with means for alignment to align the subject eye of the subject as desired. In one embodiment, the means for alignment comprises a chinrest 52 to receive the chin of the subject. The chinrest 52 is adjustable to aid in the alignment of the subject's eyes with the target spot 16 (as discussed below). The housing 10 also contains a headrest 54A and 54B to support the subject's forehead while using the machine. Headrests 54A and 54B are selected for use depending on which eye of the subject is being tested.

The housing 10 contains the basic components of the apparatus. A bleaching light source 40 is provided within the housing 10 to generate the bleaching light 42. The function of the bleaching light source 40 is as discussed above. The bleaching light source 40 may be adjusted to provide a high intensity or a low intensity bleach. Alternatively, the apparatus 1 may omit the bleaching light source 40 and the bleaching step carried out independently of the apparatus.

In the embodiment illustrated in FIG. 5A, the light source is a bank of LEDs 20 which emit a white light beam 3 and an optical element acts on the emitted white light beam 3 so that the target spot 16 is of the desired spectrum. The use of LEDs 20 as the light source may provide several advantages. First, LEDs are exceeding robust, generate almost no heat load, require little or no safety hazard protection, and are very low-cost. In addition, LEDs provide an opportunity for fine-scale intensity control via electronics, eliminating the complexity and expense of fine-scale control via neutral density wedges and other methods.

The light beam 3 is acted upon by one or more optical elements. These optical elements include, but are not limited to, directing means to direct the light beam, refining means to collimate and shape the light beam, selecting means to select the desired spectrum of the light beam, and modulating means to control the intensity of the light beam. In one embodiment, the directing means are mirrors, the refining means are shaping optics, the selecting means is an optical filter, and the modulating means is a neutral density filter or an electronic modulator. The light beam 3 is acted upon by a first mirror 24 to direct the light beam 3 to the shaping optics 25. The shaping optics 25 collimates and shapes the light beam 3 so that the target spot 16 produced is of the desired size and shape. The operation of such shaping optics 25 is well known in the art and is not discussed further herein. As the light beam 3 emerges from the shaping optics 25 it passes through an optical filter 26 so that the appropriate spectrum of light is selected for production of the target spot 16. The optical filter 26 may be a color filter. The operation of such optical filters 26 is well known in the art and is not discussed further herein. As the light beam 3 emerges from the optical filter 26, it passes through an optical splitter 30. The optical splitter 30 directs a portion of the light to a calibration detector 32. The calibration detector 32 records the characteristics of the light beam 3 (such as, but not limited to, the spectrum and intensity) and passes a portion of the light beam 3 further along the light path of the instrument. The calibration detector 32 may be a photodiode calibration detector or other calibration detector as is known in the art. As the light beam 3 emerges from the optical splitter 30, it is acted on by neutral density filter 28. The neutral density filter 28 modulates the beam of light 3 to produce the desired intensity. The use of the neutral density filter 28 will allow control of the intensity of the light beam 3 over six logs of dynamic range, with a maximum projected intensity of ~5 cd$^{-2}$. As the light emerges from the neutral density filter 28, it is further directed by one or more mirrors 24 and is ultimately projected as the target spot 16 onto a screen or other display. The location of the target spot can be located at the desired area of the subject's eye as discussed above. The directing means may be adjusted to achieve such localization. In the embodiment illustrated, the display is a screen 34. The display can be visualized by the subject.

A means for control is in communication with the various components of the apparatus 1, such as, but not limited to, the bleaching light source, the light source, the directing means, the refining means, the selecting means, and the modulating means. In addition, the means for control may be in communication with the calibration detector and the subject input means (as described below). For example, the control means may control the light emission from the light source so that the pulses of light emitted by the light source correspond to the configuration required by the test method and emissions from the bleaching light source to ensure that the percent bleaching desired is obtained. In addition, the control means could adjust the refining means, the selecting means and the modulating means to produce a light beam with the desired characteristics. Furthermore, the control means may adjust the directing means to provide desired localization of the target spot. Therefore, the means for control is capable of adjusting the parameters of the components of the apparatus as dictated by the method described. Furthermore, the control means also records the status and output of each of the components of the apparatus. For example, the control means may record the intensity of the target stimulus. The control means also records the input from the subject input means, which is used to allow the subject to input his/her responses to the target stimulus, for use in generating the threshold values. The control means may further measure and record the time elapsed during the implementation of the method (said timing to start in one embodiment immediately after the bleaching step is accomplished) and the time at which subject inputs are received from the subject input means and the time at which the various parameters of the method are changed (such as the changing intensity of the target stimulus). By comparing the timing of the subject response to the target stimulus as received from the subject input means and correlating said subject responses to the status of the parameters of the apparatus, the control means may then determine and record the threshold measurements and execute calculations required for noise reduction in the threshold measurements.

A means for comparison may be in communication with the means for control. The means for comparison may be separate from or integral with the means for control. The means for comparison may use the threshold measurements and the information from the components of the system for subsequent analysis. The means for comparison may be capable of executing calculations to fit the threshold measurements to a desired model of dark adaptation (such as, but not limited to, the one-linear, one-exponential model described above) and generating a full or partial dark adaptation model fit and/or the desired index factors from said threshold measurements and then recording and storing said information. As discussed above, the means for comparison may execute such calculations as the threshold measurements are collected, or may execute such calculations after all desired threshold measurements are obtained. The means for comparison may be an external device in communication with the control means via the internet.

The desired index factors may then be compared to corresponding index factors in a comparative database and the result recorded and stored. The comparative database index factors and comparison results may be contained within the means for comparison allowing the process to be automated or may be separate from and in communication with the means for comparison. The means for comparison may output the information to a visual display as desired. The output may be in the form of a full or partial threshold curve and dark adaptation model fit or other graphical format. In addition, the individual index factors may be displayed as well. The output may be further conveyed to a storage device or an output device, such as a printer.

The configuration of the embodiment described in FIG. 5 is for illustrative purposes only. Other configurations containing additional elements or similar substitutions for the elements described may be envisioned. In addition, the order of the elements described may be re-arranged as desired.

The apparatus 1 may also contain a means for confirming alignment of the subjects test eye. In one embodiment, such a means is an infrared camera which can be used to verify that the subject's test eye is properly aligned to view the target spot 16 and the photobleaching light 42. To aid the subject in achieving such alignment, a target fixation light 17 and a bleaching fixation light 43 may be provided (see FIG. 5B). As the subject fixes the test eye on the bleaching fixation light 43, the subject can be assured the test eye is in the proper position to receive the desired photobleaching effect. Likewise, as the subject fixes the test eye on the target fixation light 17, the subject can be assured the test eye is in the proper position to view the target spot 16. The target fixation light 17 and the bleaching fixation light 43 may be produced by additional light sources, such as LEDs incorporated at the desired locations inside the apparatus or may be projected onto the screen 34.

This design of the apparatus 1 will allow investigation of a broad range of target stimulus parameters by simple adjustment or change-out of the mirrors, shaping optics and color filters. The target spot size, location and spectrum therefore can be varied as desired by the healthcare provider. Furthermore, the intensity of the bleaching light source can also be controlled Overview of Method Implementation The use of the apparatus 1 to employ the method of the present disclosure will now be discussed. The operation of the apparatus and execution of the method can be viewed as having 5 steps: 1) aligning the subject; 2), photobleaching of the test eye; 3) monitoring recovery of visual sensitivity (i.e. scotopic recovery); 4) optionally fitting the data obtained to an appropriate model to generate the dark adaptation parameters; and 5) comparing the threshold measurements or optionally the index factors, such as the dark adaptation parameters, from the subject to a comparative database. The steps should not be construed as limiting descriptions, but are simply convenient areas for further detailed discussion. Each of these steps will be discussed in greater detail below. Furthermore, the hardware required to carry out each of these steps need not be incorporated into the test apparatus, but may be if desired.

In the alignment process, the subject is aligned by adjustment of the chin rest 52 vertically, horizontally or both vertically and horizontally. Correct positioning of the subject is achieved by viewing the subject's test eye with an infrared camera 70 mounted inside the housing 10 while the subject focuses on the target fixation light 17. The optical system is arranged such that this single step aligns the subject correctly with respect to both the bleaching light 42 and the target spot 16. The infrared camera 70 can be used as needed to confirm continued alignment of the subject.

FIG. 5B shows a view of one embodiment of the interior of the housing 10 as viewed through opening 50 and represents the view a subject would encounter on using the device.

Once alignment of the subject is achieved, the subject's test eye is subject to a bleaching protocol by exposure to the bleaching light 42. In this embodiment, the bleaching light 42 is a brief, high intensity camera flash or electronic strobe (typically 5 to 8 log scot Td/sec for 0.25 ms) that is generated while the subject is focused on the bleaching fixation light 43 to ensure the proper portion of the rhodopsin molecules of the retina is bleached. The amount of bleaching produced can be determined by the healthcare provider by varying the desired intensity of the bleaching light 42, which is controlled by the means for control as discussed above. In one embodiment, 50% to 98% of the rhodopsin molecules are bleached.

The dark adaptation measurements begin immediately after the bleaching protocol is administered by obtaining a series of threshold measurements. With the subject once again focusing on the target fixation light 17, the threshold measurements are obtained. In one embodiment, the threshold measurements are obtained using a 3-down/1-up modified staircase procedure. Starting at a first intensity (such as 4.85 cd m$^{-2}$), target spots 16 are presented on the screen 34 to the subject every 2 to 3 sec for a defined duration (such as a 200 ms pulse). If the subject does not respond to the target spot 16 (such as by activating the input means), the light intensity of the target spot 16 remains unchanged until the subject responds. If the subject indicates the target spot 16 is visible (such as by activating the input means), the light intensity of the target spot 16 is decreased for each successive pulse in 0.3 log units ("3-down") until the subject stops responding that the target spot 16 is present. After the subject indicates that the target spot 16 is invisible, the light intensity of the target spot 16 is increased for each successive pulse in steps of 0.1 log units ("1-up") until the subject responds that the target spot 16 is once again visible. This light intensity of the target spot 16 at the completion of this sequence is defined as the threshold measurement. Successive threshold measurements start with a target spot 16 light intensity 0.3 log units brighter than the previous threshold measurement. Threshold measurements are made once or twice every minute for the duration of the measurement protocol. During this process, the threshold measurements are subjected to a noise reduction protocol as discussed above. Other implementations of the staircase protocol may also be used as described above and methods other than a staircase procedure may also be employed as would be known to one of skill in the art.

To focus on rod-mediated function, a target stimulus 16 with a wavelength near the peak rod sensitivity (~500 nm) is used. Corrective lenses can be introduced between the test eye and the target spot 16 as appropriate by means of a lens holder inside the machine (not shown). The duration of the measurement protocol can be varied and may be terminated in accordance with the decision rules as discussed above.

In one embodiment, the threshold measurements are then fit to a desired model of dark adaptation. The desired model may be used to generate one or more index factors. As discussed above, the index factors may be a plurality of threshold measurements, a full or partial threshold curve or a dark adaptation parameter. Any of the dark adaptation models described herein or known to those of skill in the art may be used, such as the two-component, one-linear one-exponential model. As previously described, the initial cone-mediated (photopic) portion of the threshold curve is modeled with a linear component, and the subsequent rod-mediated (scotopic) portion of the curve is modeled with an exponential component. The comparison means may be programmed to record the appropriate parameters, to fit the data to the desired model and to automatically extract such index factors from the model. For some subjects with late ARMD, this two-component model may not provide a satisfactory fit. Insufficient sensitivity recovery after the rod-cone break will cause the exponential portion of the model to fit poorly. For cases where the two-component model proves inadequate ($R^2<0.9$), a bilinear fit can be applied to the data to accurately estimate the desired dark adaptation parameters, such as the rod-cone break, and the slope of the rod recovery will be recorded. The flexibility of employing multiple models allows tracking of disease progression more accurately than strict adherence to a single model. Alternatively, the threshold measurements may be output to the healthcare provider (in the form of a partial or full threshold curve, a dark adaptation model fit or table describing the index factors) and the healthcare provider may extract the dark adaptation parameters manually.

After the desired index factors are determined, one or more of the subject's index factors are compared to the corresponding index factors from individuals in a comparative database. In one embodiment, the subject's dark adaptation parameters are compared to a reference range of the corresponding parameters in the comparative database. The reference range may be a statistical parameter above and below the index factor in the comparative database, such as the mean of the selected index factor in the comparative database ±two standard deviations of the mean. If the subject's dark adaptation parameter falls outside the reference range, dark adaptation is considered impaired and the subject is considered to be at risk for ARMD or other disease states as described herein. If several index factors are estimated and the subject is considered abnormal on any one of the estimated index factors, dark adaptation is considered impaired and the subject is considered to be at risk for ARMD or other disease states as described herein. The comparative database is as described above. Alternatively, the threshold measurements may be directly compared to corresponding threshold measurements in the comparative database to determine dark adaptation status or disease state without going through the intermediate model fit and index factor determination.

CONCLUSION

In summary, determination of dark adaptation performed by the methods described above was shown to be a sensitive indicator of the earliest stages of ARMD. Therefore, dark adaptation can be used to identify those individuals are at-risk for ARMD and the other disease states described herein or any other disease states that impact rod photoreceptor function. Furthermore, dark adaptation can be used to indicate disease state severity and/or progression.

Given the disclosure herein, one of ordinary skill in the art may become aware of various other modifications, features, or improvements. Such other modifications, features and improvements should be considered part of this disclosure. The cited references are incorporated by reference.

EXAMPLES

Example 1

Using the reference method of the present disclosure, it was shown that impaired rod-mediated dark adaptation accurately predicts ARMD and is an early functional marker of AMD. Twenty patients (65 to 79 years old) were examined who at baseline had normal retinal health. Normal retinal health was based on a grading of photographed fundus appearance using the standardized International Classification System. During the initial baseline visit, rod-mediated dark adaptation was measured using the method described herein. The patients were classified as having normal or impaired dark adaptation at the baseline visit. Impaired dark adaptation was defined using the rod-cone break parameter as the dark adaptation parameter, with impaired dark adaptation being diagnosed when the rod-cone break parameter fell outside the reference range (±2 standard deviation of the mean) of normal healthy subjects in our comparative database. Eye health status was measured in the subsequent 4 years after the baseline visit. Medical records were examined for changes in the patient's retinal health. At the end of 4 years, 86% ($^{12}/_{14}$) of patients with impaired dark adaptation at baseline received a diagnosis of ARMD, whereas less than 17% ($^{1}/_{6}$) of patients with normal dark adaptation at baseline received a diagnosis of ARMD. These findings indicate that impaired rod-mediated dark adaptation is a risk factor for ARMD and that a method that accurately identifies impaired rod-mediated dark adaptation can be used to identify those individuals who are at risk for incident early ARMD.

Example 2

Furthermore, rod-mediated dark adaptation kinetics are markedly slowed in early ARMD patients as compared to normal age-matched subjects. Dark adaptation parameters were obtained from 20 early ARMD patients (ages 66-88) and 16 healthy subjects (ages 62-79) as described in the present disclosure. ARMD status was assigned using a standardized fundus photography grading system. On average, the time constant of rod-mediated sensitivity recovery of dark adaptation was markedly slowed in ARMD patients. In this study, the time to complete the test was on average 16 minutes longer for ARMD patients as compared to healthy individuals. Further analysis of the data revealed that 85% of the ARMD patients exhibited impaired rod-mediated dark adaptation as defined by at least one dark adaptation parameter falling outside ±2 standard deviations of the mean normal value (see Table 3). In contrast, only 20% of the healthy subjects were classified as exhibiting impaired rod-mediated dark adaptation. Significantly, cone-mediated visual sensitivity, visual acuity and contrast sensitivity were classified as impaired in only 25% of the ARMD patients, indicating impaired rod-mediated dark adaptation is a more sensitive indicator of early ARMD than visual sensitivity, visual acuity and contrast sensitivity.

Example 3

Figure 6:
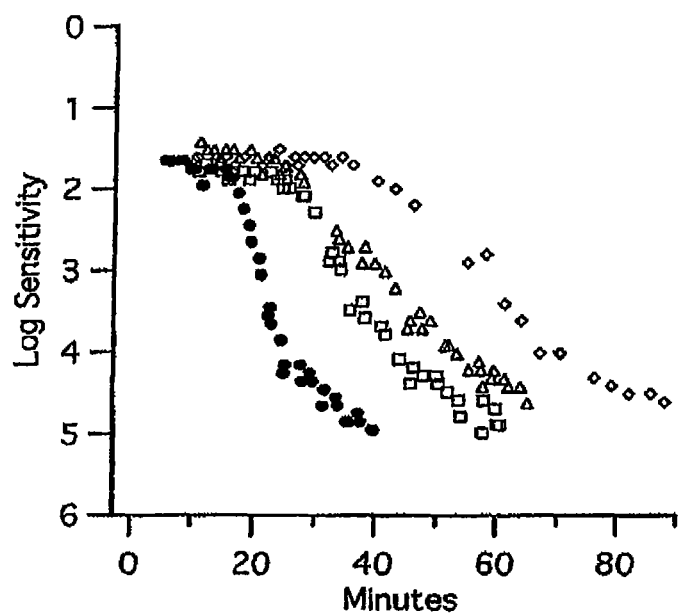
FIG. 6 illustrates dark adaptation curves generated from a normal individual (closed circle), an early ARMD patient (open square) an intermediate ARMD patient (open triangle) and a late ARMD patient (open diamond) and shows that impaired dark adaptation can be used to predict ARMD disease severity and/or progression.

In addition to identifying, those individuals at risk for ARMD, the method described herein may also be used to detect and determine differences in ARMD disease severity. Fundus photographs for a subset of ARMD patients and normal patients were sent to the Wisconsin Reading Center for grading in accordance with the Wisconsin Aging-Related Maculopathy Grading System (WARMDGS). Based on the results of the fundus photography grading, three ARMD patients (open square, triangle and diamond) and one normal patient (closed circle) were selected for examination using the method described herein. The three ARMD patients displayed different stages of ARMD progress. Patient no. 1 (open square) and no. 2 (open triangle) exhibited soft indistinct drusen with a maximum size of about 250 µm and a coverage area of about 1500 µm. However, patient no. 2 had 2-times the number of soft drusen with distribution further away from the fovea, indicating a progression of ARMD disease. Patient no. 3 (open diamond) had a number of hard drusen and a pigment epithelial detachment, indicating an additional progression of ARMD disease over patients no. 1 and no. 2. The curves and selected dark adaptation parameters generated from the threshold measurements for patients 1-3 and the normal patient were then compared. As can be seen from FIG. 6, the times for rod-mediated sensitivity recovery of dark adaptation for patient nos. 1-3 was significantly greater than the normal control. Furthermore, the time required for rod-mediated sensitivity recovery of dark adaptation was greater as the ARMD disease severity increased (with time increasing from patient no. 1 to patient no. 3). This study indicates that impaired rod-mediated dark adaptation can be used not only to determine individuals at-risk for ARMD, but to gauge ARMD disease severity and/or progression.

TABLE 1

Dark adaptation parameter differences for high bleach intensity vs. low bleach intensity

| Parameter | High Bleach Intensity (~98% bleach) | | | Low Bleach Intensity (~50% bleach) | | |
| --- | --- | --- | --- | --- | --- | --- |
| | old normal | early ARM | impairment | old normal | early ARM | impairment |
| rod-cone break | 15.41 min | 23.42 min | 52% | 7.15 min | 13.56 min | 90% |
| rod time constant | 5.32 min | 13.86 min | 161% | 5.74 min | 7.72 min | 34% |

TABLE 2

Dark adaptation parameter differences for peripheral vs. central target spot location

| Parameter | 12° inferior field | | | 5° inferior field | | |
| --- | --- | --- | --- | --- | --- | --- |
| | old normal | early ARM | impairment | old normal | early ARM | impairment |
| rod-cone break | 15.61 min | 20.48 min | 31% | 14.82 min | 24.03 min | 62% |
| rod time constant | 10.11 min | 12.49 min | 24% | 9.96 min | 16.80 min | 69% |

TABLE 3

Percentage of ARM patients exhibiting impaired rod-mediated dark adaptation (any parameter falling outside ±2 standard deviations of the normal mean value)

| Variables | Percentage |
| --- | --- |
| Kinetic Variable: | |
| Rod-cone break | 75% |
| 2cd component recovery | 56% |
| $3^{rd}$ component recovery | 0% |

TABLE 3-continued

Percentage of ARM patients exhibiting impaired rod-mediated dark adaptation (any parameter falling outside ±2 standard deviations of the normal mean value)

| Variables | Percentage |
| --- | --- |
| Time to baseline | 55% |
| Rod-mediated time constant | 65% |
| Any dark adaptation kinetics | 85% |
| Steady-State Variables: | |
| Baseline (pre-bleach) scotopic | 25% |
| Photopic sensitivity over 18° radius | 25% |
| Scotopic sensitivity over 18° radius | 20% |
| Contrast sensitivity | 35% |

What is claimed:

1. An apparatus for psychophysical measurement of dark adaptation in a test eye of a subject, said apparatus comprising:
   a. a system for generating a target stimulus of a desired spectrum and intensity;
   b. a display for displaying said target stimulus to said test eye at a desired location, said display being in communication with said system;
   c. an input device to permit said subject to input a reaction of said subject to said target stimulus;
   d. a controller in communication with said system, said display and said input device, said controller capable of controlling said system, recording at least one of the following: the reaction of said subject to said target stimulus, a time of said reaction, an intensity of said target stimulus at the time of said reaction and a spectrum of said target stimulus at the time of said reaction, and determining at least one threshold measurement from said recording; and
   e. extracting a rod intercept from the at least one threshold measurement.

2. The apparatus of claim 1 further comprising fitting said at least one threshold measurement to a dark adaptation model and extracting the rod intercept from the dark adaptation model.

3. The apparatus of claim 1 where the controller compares one or more of said at least one threshold measurement or said rod intercept of said subject to corresponding values from a comparative database comprising a population of individuals, said controller storing said comparative database and the results of said comparing.

4. The apparatus of claim 1 where said system is an optical system and said optical system comprises:
   a. a first light source for generating said target stimulus, said first light source emitting a defined spectrum, or emitting a broad spectrum and said apparatus further comprising at least one optical element to select a portion of the broad spectrum to generate a defined spectrum or a combination of the foregoing; and
   b. at least one neutral density filter, at least one electronic modulator or a combination of the foregoing to control the intensity of the target stimulus.

5. The apparatus of claim 1 where the display is a screen, a diffuser, an LED display, a liquid crystal display, a plasma display, or a CRT display or a combination of the foregoing.

6. The apparatus of claim 4 further comprising at least one optical element selected from the group consisting of: a shaping optic to shape the target stimulus, a directing optic to direct the target stimulus to said display, an optical splitter and a calibration detector.

7. The apparatus of claim 1 where said system is an electronic system.

8. The apparatus of claim 1 further comprising a second light source for generating a bleaching light.

9. The apparatus of claim 8 where said second light source is a photographic flash or an electronic strobe.

10. The apparatus of claim 8 where the bleaching light inactivates 50% to 100% of the rhodopsin molecules in said test eye.

11. The apparatus of claim 8 where said bleaching light has an intensity from 5.36 log scotopic Trolands/sec to 7.65 log scotopic Trolands/sec.

12. The apparatus of claim 1 where said at least one threshold measurement is selected from the group consisting of: a plurality of selected threshold measurements, a partial threshold curve and a full threshold curve.

13. The apparatus of claim 1 further comprising an alignment element to ensure the target eye of said subject is properly aligned.

14. The apparatus of claim 13 where said alignment element comprises at least one of an adjustable chinrest, a target fixation light, a bleaching fixation light or a camera to ensure and monitor proper alignment of said test eye, said target fixation light.

15. The apparatus of claim 4 where the first light source is at least one light emitting diode.

16. The apparatus of claim 15 where said at least one light emitting diode emits a light having a spectrum effective in stimulating the rod photoreceptors of said test eye.

17. The apparatus of claim 16 where said spectrum comprises at least one wavelength from 400 nm to 550 nm.

18. The apparatus of claim 15 where said at least one light emitting diode emits a broad spectrum light and the at least one optical element selects a spectrum effective in stimulating the rod photoreceptors of said test eye.

19. The apparatus of claim 18 where said broad spectrum light is a white light.

20. The apparatus of claim 3 where said comparative database is stratified with respect to stratification criteria and said stratification criteria are used to select a defined group of individuals within said comparative database for use in said comparison step.

21. The apparatus of claim 20 where said stratification criteria is a dark adaptation status, a risk factor or a demographic factor.

22. The apparatus of claim 21 where said risk factors are selected from the group consisting of: age, smoking status, body mass index and status with regard to a disease state.

23. The apparatus of claim 21 where said demographic factors are selected from the group consisting of age, ethnicity and gender.

24. The apparatus of claim 3 where the comparative database consists of individuals from 20 to 85 years of age.

25. The apparatus of claim 3 where the comparative database consists of individuals from 20 to 45 years of age.

26. The apparatus of claim 3 where the comparative database consists of individuals that are not age-matched to the subject.

27. The apparatus of claim 3 where the comparative database is purged of individuals who are determined to develop impaired dark adaptation status within a defined period of time after inclusion in said comparative database.

28. The apparatus of claim 20 where said defined group is selected based on at least one defining characteristic of said subject.

29. The apparatus of claim 1 where the controller further comprises a noise reduction protocol and said at least one threshold measurement is subject to said noise reduction protocol.

30. The apparatus of claim 29 where the noise reduction protocol is a non-destructive noise reduction protocol.

31. The apparatus of claim 30 where the non-destructive noise reduction protocol is threshold guidance, curve guidance or a combination of the foregoing.

32. The apparatus of claim 31 where threshold guidance comprises comparing a presumptive threshold Measurement to a base threshold measurement or a model-fit of said base threshold measurement, determining if said presumptive threshold measurement falls within a predetermined window of said base threshold measurement or model-fit and discarding said presumptive threshold measurements that do not fall within said window or replacing said presumptive threshold measurements that do not fall within said window.

33. The apparatus of claim 31 where said curve guidance comprises subjecting said at least one threshold measurement to a statistical function of a defined width anchored to said at least one threshold measurement or a model-fit of said at least one threshold measurement, thereby obtaining at least one threshold value, and discarding those of said threshold values that fall outside of said width.

34. The apparatus of claim 3 where said controller uses the results of said comparison to determine a dark adaptation status of said subject.

35. The apparatus of claim 34 where said dark adaptation status is considered impaired if one or more of said at least one threshold measurement or said rod intercept determined for said subject meets an impairment criterion.

36. The apparatus of claim 35 where said impairment criterion is met when said comparing is conducted using a defined group from said comparative database consisting of healthy individuals and one or more of said at least one threshold measurement or said rod intercept determined for said subject falls outside of a reference range of corresponding measurements from said defined group.

37. The apparatus of claim 35 where said impairment criterion is met when said comparing step is conducted using a defined group from said comparative database consisting of individuals diagnosed with a disease state and one or more of said at least one threshold measurement or said rod intercept determined for said subject falls within a reference range of said corresponding measurements from said defined group.

38. The apparatus of claim 36 where said reference range is selected from the group consisting of the mean plus or minus two standard deviations of the mean, cut points, receiver operating curves, and confidence intervals.

39. The apparatus of claim 37 where said reference range is selected from the group consisting of the mean plus or minus two standard deviations of the mean, cut points, receiver operating curves, and confidence intervals.

40. The apparatus of claim 35 where said status of impaired dark adaptation of said subject indicates said subject is at risk for a disease state selected from the group consisting of age related macular degeneration, vitamin A deficiency, Sorsby's Fundus Dystrophy, late autosomal dominant retinal degeneration, retinal impairment related to diabetes and diabetic retinopathy.

41. The apparatus of claim 35 where said status of impaired dark adaptation of said subject indicates said subject is suffering from a disease state selected from the group consisting of age related macular degeneration, vitamin A deficiency, Sorsby's Fundus Dystrophy, late autosomal dominant retinal degeneration, retinal impairment related to diabetes and diabetic retinopathy.

42. The apparatus of claim 35 where said controller uses at least one of the results of said comparison and the status of impaired dark adaptation to suggest a diagnosis that said subject is at risk for a disease state selected from the group consisting of age, related macular degeneration, vitamin A deficiency, Sorsby's Fundus Dystrophy, late autosomal dominant retinal degeneration, retinal impairment related to diabetes and diabetic retinopathy.

43. The apparatus of claim 35 where said controller uses at least one of the results of said comparison and the status of impaired dark adaptation to suggest a diagnosis that said subject is suffering from a disease state selected from the group consisting of age related macular degeneration, vitamin A deficiency, Sorsby's Fundus Dystrophy, late autosomal dominant retinal degeneration, retinal impairment related to diabetes and diabetic retinopathy.

44. The apparatus of claim 34 where said dark adaptation status is determined in less than 20 minutes.

45. The apparatus of claim 34 where said dark adaptation status is determined in less than 10 minutes.

46. The apparatus of claim 34 where said dark adaptation status is determined with at least 80% specificity or 80% sensitivity.

47. The apparatus of claim 34 where said dark adaptation status is determined with at least 90% specificity or 90% sensitivity.

* * * * *

UNITED STATES PATENT AND TRADEMARK OFFICE
CERTIFICATE OF CORRECTION

PATENT NO. : 9,504,379 B2  
APPLICATION NO. : 14/706536  
DATED : November 29, 2016  
INVENTOR(S) : Gregory R. Jackson et al.

Page 1 of 1

It is certified that error appears in the above-identified patent and that said Letters Patent is hereby corrected as shown below:

In the Specification

Column 1 Line 4, insert the following:
--GOVERNMENT FUNDING
This invention was made with government support under grant number AG004212 awarded by the National Institutes of Health. The government has certain rights to the invention.--

Signed and Sealed this  
Seventh Day of April, 2020

Andrei Iancu  
*Director of the United States Patent and Trademark Office*